(12) United States Patent
Nissilä

(10) Patent No.: US 6,443,904 B2
(45) Date of Patent: Sep. 3, 2002

(54) DETERMINATION OF STRESS LEVEL OF FITNESS EXERCISE

(75) Inventor: Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/810,698

(22) Filed: Mar. 16, 2001

(30) Foreign Application Priority Data

Mar. 17, 2000 (FI) .............................................. 20000630

(51) Int. Cl.⁷ ................................................ A61B 5/02
(52) U.S. Cl. ...................................... 600/483; 600/508
(58) Field of Search .............................. 600/483, 481, 600/485, 440, 500, 501, 502, 503, 508, 509, 529, 532

(56) References Cited

U.S. PATENT DOCUMENTS

| 3,675,640 A | | 7/1972 | Gatts |
| 4,367,752 A | * | 1/1983 | Jimenez et al. ............ 377/24.2 |
| 4,566,461 A | * | 1/1986 | Lubell et al. .............. 377/24.2 |
| 5,626,144 A | | 5/1997 | Tacklind et al. |
| 5,810,722 A | | 9/1998 | Heikkilä |
| 5,853,351 A | | 12/1998 | Maruo et al. |
| 5,894,041 A | * | 4/1999 | Golosarsky et al. ........ 600/509 |

FOREIGN PATENT DOCUMENTS

EP          0 590 634          4/1994

* cited by examiner

*Primary Examiner*—Kevin Shaver
*Assistant Examiner*—Navin Natnithithadha
(74) *Attorney, Agent, or Firm*—Hoffmann & Baron, LLP (57) ABSTRACT

A heart rate monitor includes a measuring means for measuring the heart rate of a person during a fitness exercise, and a calculation unit for forming the value of one or more stress parameters from the heart rate measured during the fitness exercise. The calculation unit is arranged to compare the stress parameter value during the fitness exercise with a threshold value formed for the stress parameter before the fitness exercise. The heart rate monitor also includes a display means for showing exceeding of the threshold parameter to the user during the fitness exercise. The calculation unit is arranged to use the value of expiratory flow measured from the person before the fitness exercise for forming the threshold value of the stress parameter.

20 Claims, 5 Drawing Sheets

DETERMINATION OF STRESS LEVEL OF FITNESS EXERCISE

BACKGROUND OF THE INVENTION

1. Field of the Invention

The invention relates to sports and medicine, particularly to applications in which the capacity of a person is controlled during a fitness exercise according to a value of respiratory flow measured before the fitness exercise.

During a fitness exercise the ventilation frequency, i.e. inspiration and expiration, increases as the workload increases. Normally the respiratory capacity of a person is always so good that is does not limit the fitness exercise even at heavy workload, but the oxygen uptake and removal of carbon dioxide are sufficient for metabolism. The respiratory capacity may, however, limit exercising if the person suffers from a disease of respiratory organs or respiratory bronchioles, such as asthma. Persons suffering from exercise induced asthma may experience dyspnoea and stridor during a fitness exercise because due to asthma their respiratory organs may be inflamed and swollen. The number of asthmatics is increasing in the West, being already about 2 to 4% of the population.

2. Description of the Prior Art

The basis for treating asthma and other respiratory diseases is good physical condition which prevents serious complications and helps to cope with difficult situations. The general instructions for improving the physical condition cannot be applied to asthmatics because their respiratory flow values vary considerably. In practice, asthmatics therefore have to determine their respiratory flow before each fitness exercise and decide on the exercise workload on the basis of the respiratory flow. U.S. publication No. 5,626,144 discloses a PEF meter (Peak Expiratory Flow) for measuring the respiratory flow. By blowing into the meter the user finds out the current expiratory flow. On the basis of the measured value the person can decide whether to take medication before a fitness exercise and plan the exercise workload at a broad level. U.S. publication No. 3,675,640 describes a solution between a variable describing the person's capacity, such as inhaled oxygen or exhaled carbon dioxide, and physical stress. In the solution described in the publication the patient's maximal capacity is determined according to measurement results obtained during a fitness exercise in a clinical environment and results achieved by a healthy person.

The prior art method of determining the capacity is designed for hospitals and requires a complex and expensive apparatus. Consequently, the method cannot be applied in everyday sports.

SUMMARY OF THE INVENTION

The object of the invention is to provide an improved method and an apparatus implementing the method for determining the stress level of a fitness exercise. This is achieved with the following method of controlling a fitness exercise performed by a person. The method comprises measuring the person's heart rate information during the fitness exercise and informing the person if, during the fitness exercise, the value of a stress parameter formed from the measured heart rate information exceeds a threshold value formed for the stress parameter before the fitness exercise. In the method the threshold value of the stress parameter is formed for the fitness exercise using the value of the person's expiratory flow.

The invention also relates to a heart rate monitor which comprises means for measuring the heart rate of a person during a fitness exercise, a calculation unit for forming the value of one or more stress parameters from the measured heart rate during the fitness exercise, the calculation unit being arranged to compare the value of the stress parameter during the fitness exercise with a threshold value formed for the stress parameter before the fitness exercise, the heart rate monitor further comprising display means for showing exceeding of the threshold value of the stress parameter to the person during the fitness exercise. The calculation unit is arranged to use the value of the person's expiratory flow measured for the fitness exercise for forming the threshold value of the stress parameter.

The invention relates to a method and an apparatus for determining the optimal exercise level of a person and for controlling it during a fitness exercise. The solution is particularly suitable for a fitness exercise performed by a person who suffers from a disease of respiratory organs, such as asthma. In this description a fitness exercise refers to a physical exercise performed at a heart rate level of at least about 20 heart beats per minute over the person's heart rate at rest.

A method according to a preferred embodiment of the invention comprises measuring the heart rate information of a person during a fitness exercise. The heart rate information to be measured refers to heart rate parameters that can be measured from heartbeats, such as the average heart rate per minute, standard deviation of the heart rate, change rate of the heart rate or other similar parameters that can be calculated from the heart rate. One or more of the above-mentioned heart rate parameters are used as a stress parameter which describes the exercise workload. A threshold value which should not be exceeded during the fitness exercise is set for the stress parameters. In an embodiment the person's stress level during the fitness exercise is used as the stress parameter in addition to a heart rate parameter or instead of it. The stress level is formed using one or more of the following parameters: one or more heart rate parameters, one or more physiological parameters which describe the person's physiological properties, one or more stress parameters which describe the exercise workload.

The threshold value of the stress parameter is formed before the fitness exercise, and preferably the threshold value is re-formed before each fitness exercise The person's current maximal expiratory flow is used for forming the threshold value. In a preferred embodiment the expiratory flow is measured with a PEF meter. In an embodiment the measured PEF value is compared with the reference value of expiratory flow, and the threshold value of the stress parameter is formed on the basis of this comparison. The reference value of expiratory flow means e.g. the person's maximum value of expiratory flow. The reference value can also be formed on the basis of tabulated information or by means of a neural network using one or more physiological parameters. The method according to the invention is preferably implemented by a heart rate monitor into which the PEF value measured by the user is fed before the fitness exercise. In an embodiment the heart rate monitor forms the reference value of expiratory flow, which is read from a table included in the heart rate monitor or formed by means of a neural network using the physiological parameters to be fed into the heart rate monitor. During the fitness exercise the heart rate monitor measures the heart rate, and in an embodiment one or more of the following items are presented on the display of the heart rate monitor: heart rate parameter, threshold value of the heart rate parameter, stress level, threshold value of the stress level. Furthermore, if the user exceeds the threshold value of the stress parameter during the fitness exercise, the heart rate monitor gives a sound signal or a voice message, informs the user of exceeding by displaying information on the display of the heart rate monitor or with touch information, such as vibration or the like, in which case the user can reduce the exercise workload or finish the exercise.

In an embodiment of the invention the apparatus implementing the method according to the invention is a heart rate monitor. The heart rate monitor is a device employed in sports, which measures human heart rate information from an electrical impulse transmitted by the heart, from the pressure produced by the heart beat on an artery or optically from the blood movement in an artery. The structures of the heart rate monitors available vary. There are, for example, heart rate monitors which comprise an electrode belt to be fitted around the user' chest and a wrist-worn receiver unit. The electrode belt measures the heart rate and transmits information on it to the receiver unit, which calculates heart rate parameters on the basis of the information received. Often, the receiver unit, i.e. the wrist monitor, also comprises a display for showing the heart rate information and other heart rate parameters formed in the heart rate monitor to the exerciser. In the present invention, information on the stress level during exercise and/or the threshold value corresponding to it are preferably shown on the display. The heart rate monitor can also be a one-piece device in which the measurement, processing and display are located in the electrode belt to be fitted around the chest, and thus there is no need to transmit the information to a separate receiver unit. Further, the structure of the heart rate monitor can be such that it only comprises a wrist-worn monitor which operates without the electrode belt to be fitted around the chest, measuring the heart rate from the vessel pressure or optically.

The heart rate monitor preferably also comprises means for feeding the measured value and the reference value of expiratory flow, user-specific physiological information and information on the exercise workload. The feeding means can be, for instance, a keypad of the heart rate monitor, display equipment that supports feeding of information, a speech controller, an optical feeding device, a telecommunications port for external control or the like.

The functions required by the method of the invention, such as calculation operations, a neural network or the like, are preferably implemented by software for a general-purpose processor. The functions can also be implemented as ASIC, with separate logic components or in a corresponding manner.

An advantage of the invention is that it provides an improved method of determining the optimal level for a fitness exercise to be performed by a person who suffers from a disease of respiratory organs before the fitness exercise. A further advantage of the invention is that it enables monitoring during the fitness exercise that the exercise workload remains at a suitable level for the person in question.

BRIEF DESCRIPTION OF THE DRAWINGS

In the following the invention will be described in greater detail with reference to the accompanying drawings, in which.

DETAILED DESCRIPTION OF THE INVENTION

Figure 1A:
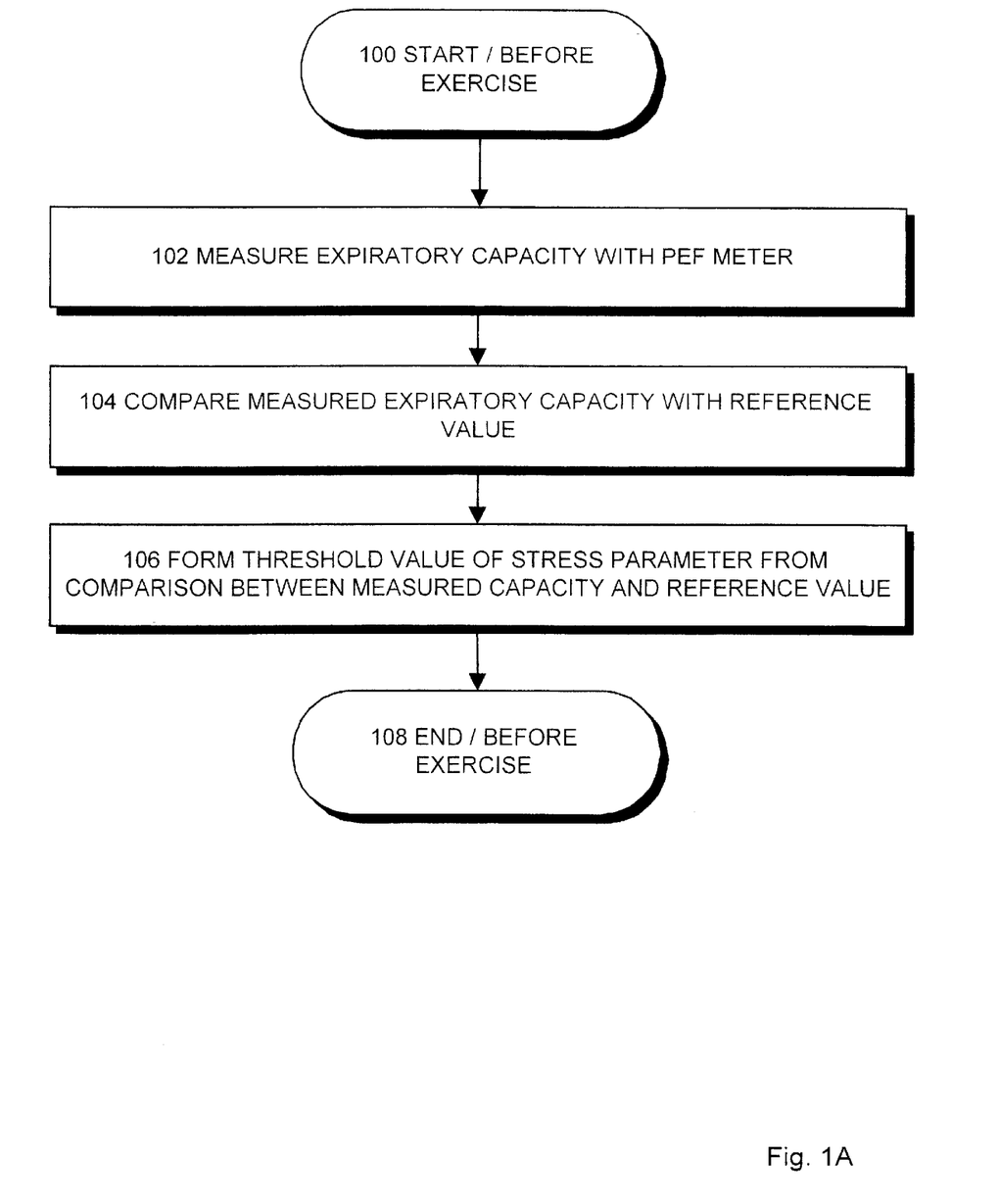
FIG. 1A is a block diagram illustrating an embodiment of the method according to the invention.

The invention will be described in the following by means of preferred embodiments with reference to FIGS. 1 to 4. FIG. 1A illustrates a preferred embodiment of the method according to the invention, showing the steps that are carried out before a fitness exercise. In step 102 the expiratory flow of a person is measured with a PEF meter. The PEF is typically measured when the person exhales at maximum effort after maximal inhalation. In the PEF meter the intensity of the air flow caused by blowing can be indicated with a spring or using a liquid crystal display. The peak flow is expressed as liters/minute and it usually varies between 300 to 700 l/min, depending on the person's physiological properties.

Figure 2:
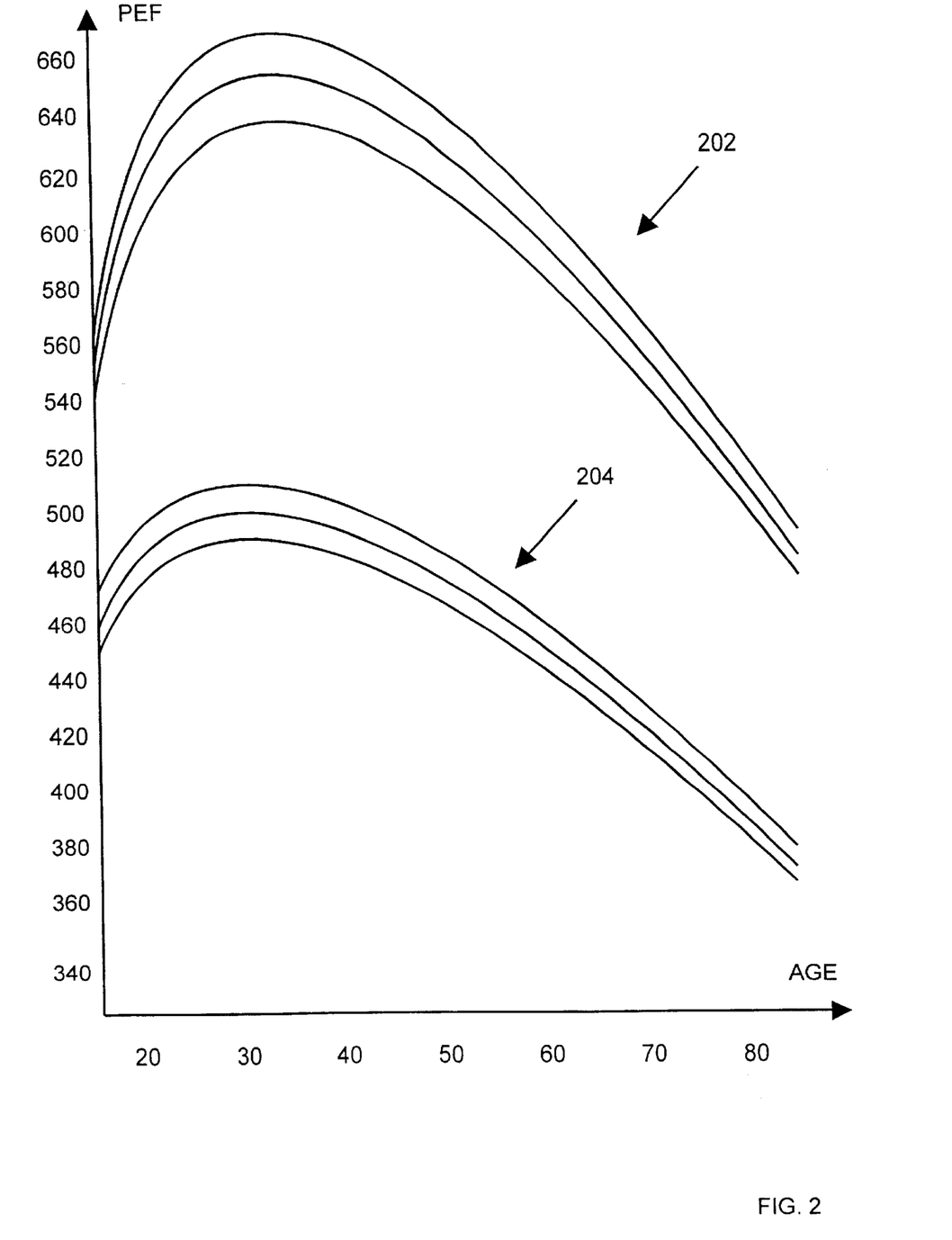
FIG. 2 illustrates reference values of expiratory flows as a function of physiological parameters.

In step 104 the measured expiratory flow is compared with the reference value. The comparison is preferably performed by a heart rate monitor, into which the measured expiratory flow is fed. The reference value is formed e.g. by reading it from a table included in the heart rate monitor or by calculating it by means of a neural network. At least one of the following physiological parameters is used for forming the reference value: age, gender and height. In FIG. 2 the vertical axis represents the reference value of the person's expiratory flow as a function of the person's age shown on the horizontal axis. The figure illustrates separate graphs for men and women, the upper graph 202 being for men and the lower graph 204 for women. The graphs 202 to 204 comprise separate curves for persons of different heights; for example, the topmost curve in the graph 202 for men describes, as a function of age, the maximum values of expiratory flow for a man of a height of 190 cm, the curve in the middle for of a man of a height of 180 cm and the lowest curve for a man of a height of 170 cm. The value corresponding to the person's maximal expiratory flow shown in FIG. 2 can also be formed e.g. in such a manner that the person measures his/her PEF value in the morning and evening during one month and stores his/her personal maximum value. In an embodiment of the invention the personal maximum flow measured as described above is fed as a reference value into the heart rate monitor, which compares the measured expiratory flow with the reference value. In step 104 comparison means e.g. calculation of the percentage, i.e. how many percents the measured value is of the reference value. It is clear that the above-mentioned percentage can also be formed otherwise than by calculating it in the heart rate monitor, in which case only the result of comparison is fed into the heart rate monitor.

In step 106 the threshold value of the stress parameter is formed on the basis of the comparison result obtained in step 104. Here the stress parameter refers to the heart rate level or the stress level, but the heart rate variation, for example, or a similar parameter that can be derived from the heart beat frequency can also be used as the stress parameter. If the heart rate is used as the stress parameter, the threshold value of the heart rate is calculated by formula (1), for example:

$$HR_{LIMIT} = comp\ \%^* \ HR_{REF}, \qquad (1)$$

where $HR_{LIMIT}$ represents the threshold value of heart rate, comp % represents the comparison value of expiratory flows and $HR_{REF}$ represents the reference value of heart rate. The reference value $HR_{REF}$ of heart rate is preferably set so that it controls the stress level of the fitness exercise as desired. For example, if the person wants to exercise at the maximum heart rate, the person's maximum heart rate is used as the reference heart rate. If the person wants to exercise at a heart rate level of 160, 160 is used as the reference heart rate, which should not be exceeded during the exercise. Instead of the upper limit, the threshold value $HR_{LIMIT}$ of heart rate in the above formula (1) can also mean the lower limit of heart rate below which the heart rate should not drop during the exercise. If the $HR_{LIMIT}$ is 120, for example, the threshold value is exceeded if the person's heart rate drops below the threshold value 120. It is clear that instead of one threshold value, the $HR_{LIMIT}$ can refer to a range within which the person's heart rate should remain during the exercise. Thus the $HR_{LIMIT}$ can be (130+/−10) beats, in which case the threshold value is exceeded when the heart rate rises over 140 or drops below 120.

In an embodiment of the invention the heart rate monitor checks whether the comparison value is allowable. If the comparison value indicates that the respiratory flow is only 50% or less of the person's reference value, the user is informed that the comparison value is too low for performing a fitness exercise due to health reasons or that exercising is not recommendable. The limit value, i.e. the health-related reference value (50% above), for the above-mentioned check is obtained from a doctor and can be fed into the heart rate monitor using its feeding means.

In an embodiment of the invention the reference heart rate $HR_{REF}$ is formed by means of pre-determination where the workload increases gradually. This is preferably performed before each fitness exercise. During the pre-determination the user e.g. walks slowly for two minutes, two minutes at a faster rate and another two minutes at a faster rate. During the pre-determination the user's heart rate and heart rate variation, i.e. the standard deviation of the heart rate, are measured as the workload increases gradually. The two-minute periods are repeated until the heart rate variation drops below a threshold value, such as 4 ms, as the heart rate increases. The heart rate corresponding to the above-mentioned point is used as the reference heart rate $HR_{REF}$. The purpose of the pre-determination is to determine the person's activity level and how stressed his/her system is on the day in question. Instead of the reference heart rate, the pre-determination can also be used for adjusting the reference values of the user's respiratory flows. For example, if the pre-determination indicates that the person is stressed due to an exercise performed at a heavy workload on the previous day, the reference values of respiratory flow are correspondingly set to a lower level. The pre-determination described above is at least partly included in the fitness exercise because the above-mentioned point where the heart rate variation drops below the threshold value is achieved at a heart rate level which is approximately 65% of the maximum heart rate, i.e. at a heart rate level of about 130.

In an embodiment the maximum heart rate is always used as the reference heart rate $HR_{REF}$. In the above-mentioned embodiments the maximum heart rate can be formed in various ways, e.g. by calculating it by the formula (220−age), by measuring the heart rate at the maximal stress, by estimating it, by determining it by means of a neural network, into which at least one physiological parameter is fed, or by some other prior art manner. The above-mentioned stress level used as the stress parameter refers to a variable which is formed during the fitness exercise using one or more of the following parameters: one or more heart rate parameters formed from the person's heart rate information, one or more physiological parameters, one or more parameters describing the exercise workload, such as running speed, swimming speed, resistance of the exercise bike or the like. The stress level value is preferably formed in the heart rate monitor by means of a neural network during the fitness exercise. The stress level is measured e.g. as workload/time unit, in which case the stress level gives an idea of the cumulative stress experienced by the person during the fitness exercise.

Figure 1B:
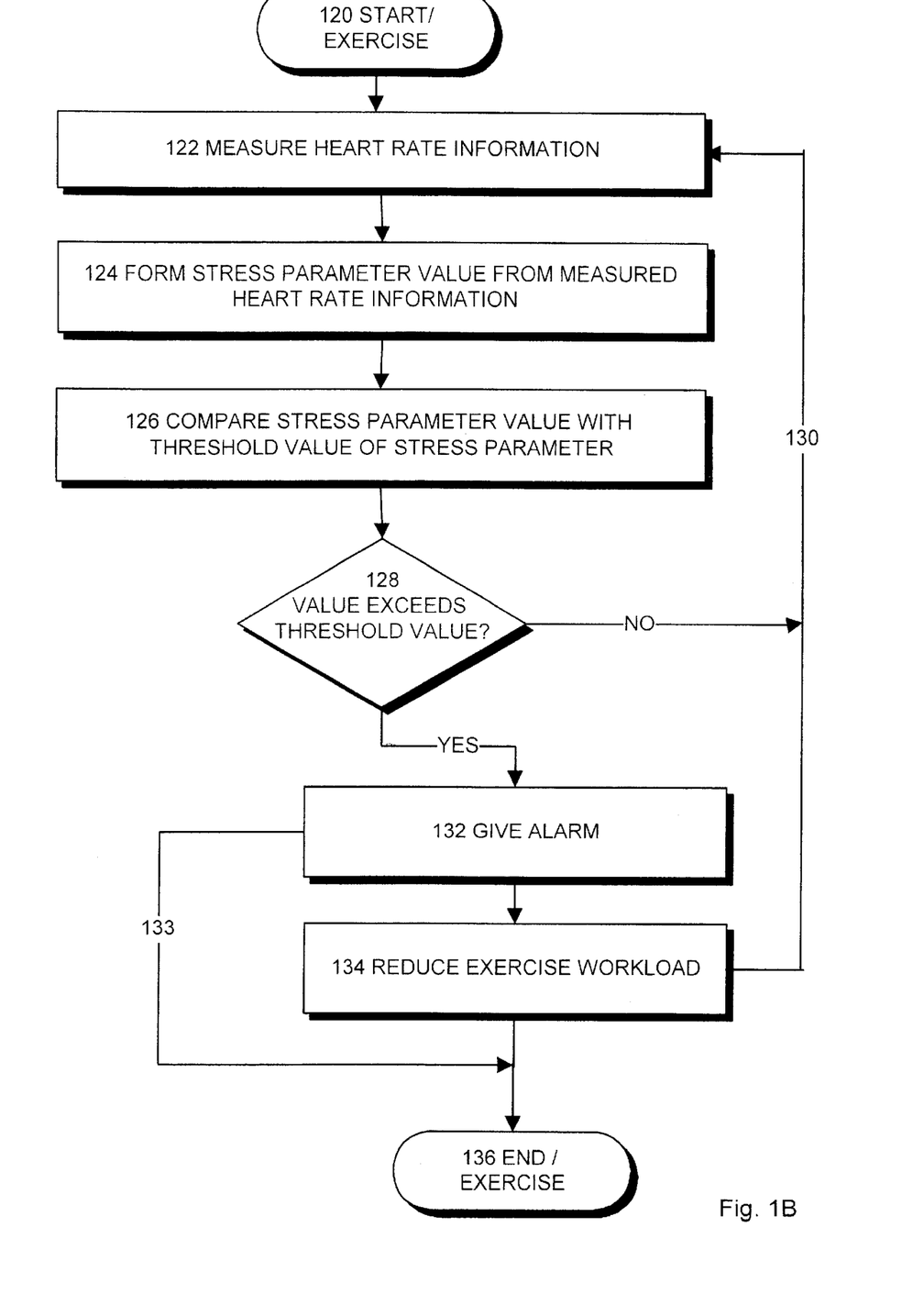
FIG. 1B is a block diagram illustrating an embodiment of the method according to the invention.

In the following the invention will be described with reference to FIG. 1B, which illustrates procedures performed during the fitness exercise. In step 122 a heart rate monitor measures information on the person's heart rate. Measurement of heart rate information means measurement of the heart rate, i.e. heart beat frequency. The heart rate can also be used for calculating other heart rate parameters, such as the standard deviation of heart rate or the change rate of heart rate. In step 124 a value is calculated for the stress parameter from the heart rate information. At its simplest the stress parameter is the heart rate, in which case no measures are required in step 124. If the stress level is used as the stress parameter, the stress level value is calculated continuously as a function of heart rate by means of a neural network, for example. In step 126 the stress parameter value formed above is compared with the threshold value of the stress parameter which was formed in step 106. In practice the stress parameter value is compared with the threshold value periodically in step 126, e.g. always when the heart rate is calculated, e.g. once in a second. In step 128 the process continues as follows on the basis of the comparison result: if the threshold value was not exceeded, measurement of the heart rate continues according to step 130; if the threshold value was exceeded, an alarm is given in step 132. The alarm is given e.g. by means of the heart rate monitor as flashing information on the display of the heart rate monitor, as a voice or speech message, as vibration or in another similar manner. There are two ways to react to an alarm: the workload is decreased according to step 134, after which exercising is continued and the heart rate measured according to step 130. Alternatively, the fitness exercise is finished according to step 133. This alternative comes into question particularly when the stress level is used as the stress parameter.

Figure 3A:
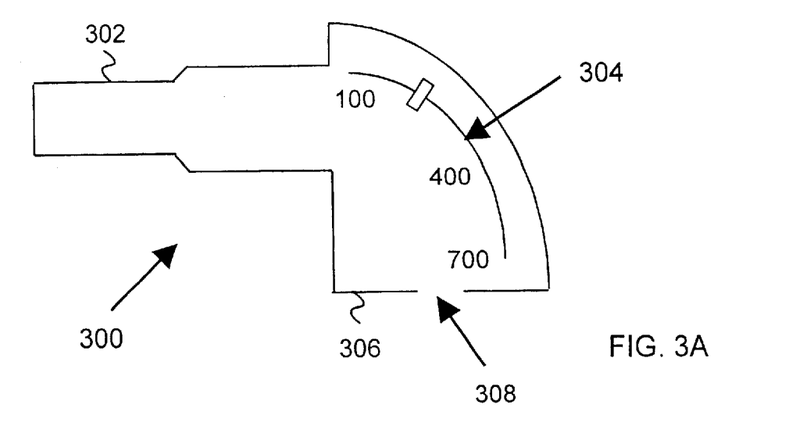
FIG. 3A illustrates a PEF meter.
Figure 3B:
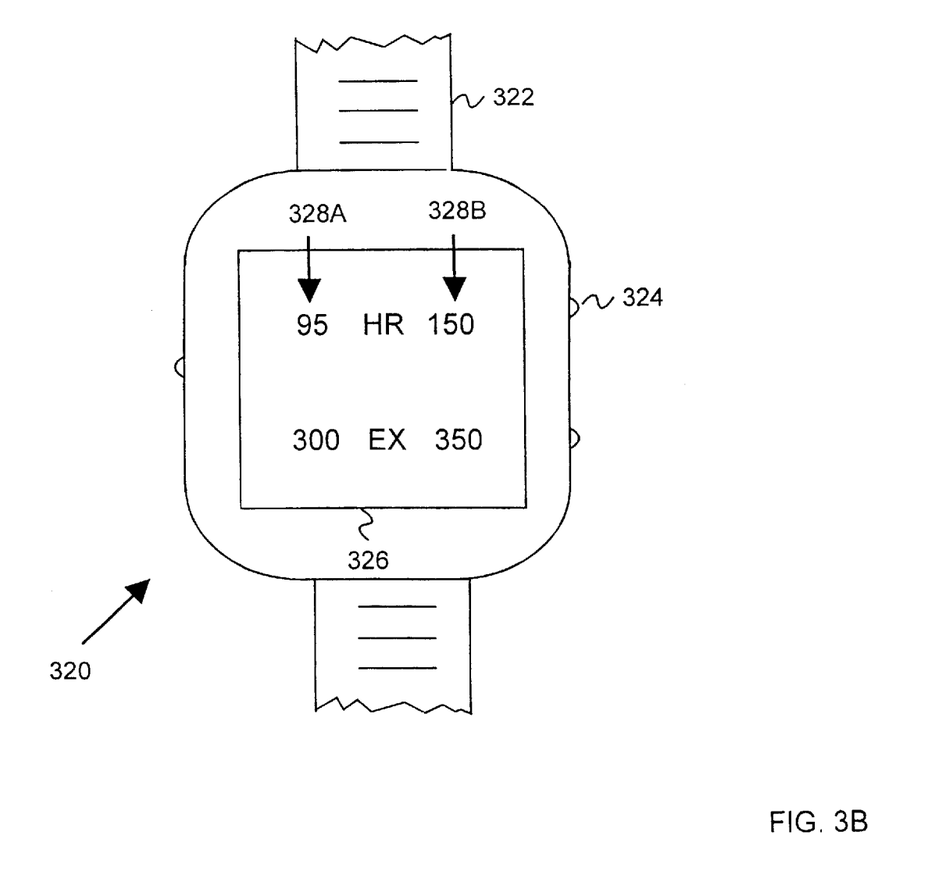
FIG. 3B illustrates a heart rate monitor according to an embodiment of the invention.

FIGS. 3A and 3B illustrate an embodiment of the apparatus according to the invention. FIG. 3A shows a PEF meter 300 which comprises a mouthpiece 302 against which the user places his/her mouth for measurement of the expiratory flow. Air passes from the mouthpiece 302 into the air container 306 of the PEF meter 300 and exits through an exit opening 308. The air that passes through the air container 306 moves a spring indicator 304 which shows the person's maximal expiratory flow. FIG. 3B illustrates an embodiment of the heart rate monitor 320. The heart rate monitor 320 comprises a wrist strap 322 for attaching it to the wrist. The heart rate monitor 320 also comprises a keypad consisting of one or more keys 324 for feeding the information needed to control the fitness exercise. The information to be fed comprises e.g. the value of the person's expiratory flow measured by the PEF meter shown in FIG. 3A or the person's physiological parameters, such as age, gender or height. From the physiological information fed the heart rate monitor 320 calculates a reference value for expiratory flow and forms a comparison value by comparing it with the measured expiratory flow. The heart rate monitor calculates the comparison value and the person's maximum heart rate which can be estimated from the physiological parameters. Using these values, the heart rate monitor forms threshold values for the heart rate and the stress level according to formula (1). The heart rate monitor 320 further comprises a display 326 for presenting stress parameter values and the corresponding threshold values during the fitness exercise, such as the heart rate 328A and its threshold value 328B, the stress level (EX) value (300) and the corresponding threshold value (350). If either one of the threshold values is exceeded, the sound signaling device of the heart rate monitor gives a sound signal which tells the user that he/she has exceeded the threshold value. As a result of exceeding of the threshold value the user can either continue the exercise at a lower heart rate or finish the exercise.

The heart rate monitor that implements the steps of the invention will be described by an example with reference to FIG. 4. The heart rate of an exercising person is measured by means of a transmitter electrode belt fitted around the chest. The transmitter electrode belt is illustrated by the entity formed by components 400A to 408. The measured heart rate is preferably transmitted inductively to a wrist-worn receiver, which is illustrated by the entity formed by components 420 to 432. The entity formed by the transmitter electrode belt and the receiver is called a heart rate monitor.

The transmitter electrode belt measures the heart rate by means for measuring the heart rate 400A and 400B. The measuring means are e.g. electrodes. The heart rate monitor comprises at least two electrodes but more can also be used. From the electrodes 400A and 400B the heart rate signal is applied to an EKG preamplifier 402, from which the signal is transferred via an AGC amplifier 404 and a power amplifier 406 to a transmitter 408. The transmitter 408 is preferably implemented as a coil which sends the heart rate information 410 inductively to a receiver, such as a wrist-worn receiver unit or to an external computer. One 5 kHz burst 410A corresponds to one heart beat, for instance, or a cluster of bursts 410A to 410C may correspond to one beat. The intervals 412A to 412B between the bursts 410A to 410C can be equal or different in duration. In addition to inductive transmission, information can be transmitted between the electrode belt and the receiver unit optically or via a conductor, for instance. In an embodiment the receiver unit 420 to 432, such as the wrist-worn receiver, comprises a receiver coil 420, from which the received signal is applied through a signal receiver 422 to a central processor 424, which coordinates the operation of different parts of the receiver unit. The receiver unit preferably also comprises a memory 428 for storing the heart rate information and other data relevant to the invention, such as expiratory flow values. The heart rate monitor further comprises display means 326 for presenting the stress parameter and its threshold value. The display means 326 is e.g. a display or a speech controller. The heart rate and its threshold value as well as the stress level and its threshold value, for example, are presented on the display. In an embodiment of the invention the display means 326 refers to a sound signaling device for giving a sound signal when the threshold value of the stress parameter is exceeded. The display means 326 can also be a voice messaging device or a vibrating device. It is clear that several display means can be used simultaneously, e.g. the sound signaling device and the display.

Figure 4:
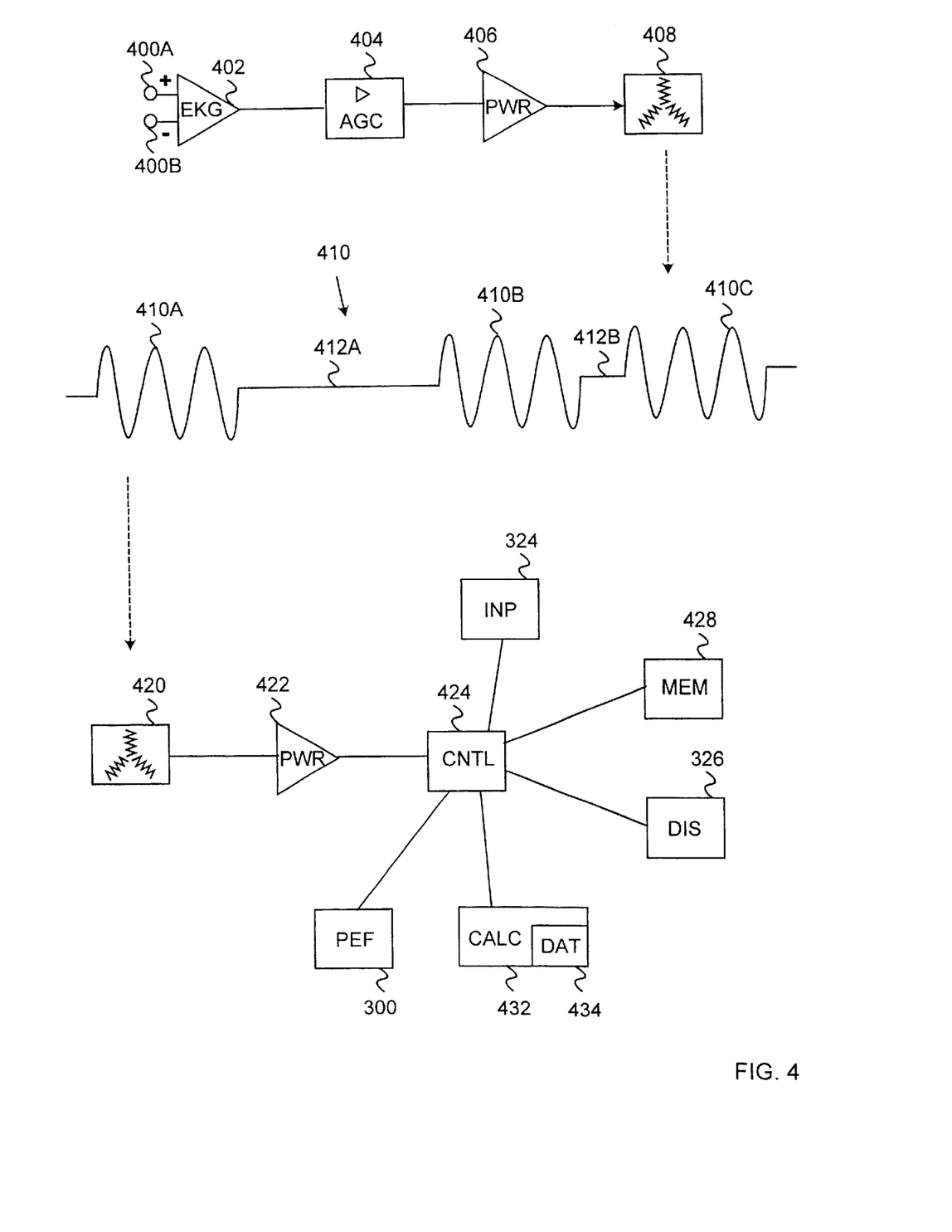
FIG. 4 illustrates an embodiment of the apparatus according to the invention.

The heart rate monitor and its receiver according to an embodiment shown in FIG. 4 further comprise a calculation unit 432 for forming the reference value of expiratory flow by means of physiological parameters. For forming the reference value the calculation unit can use tabulated reference values included in an information unit 434 or reference values formed by a neural network. In an embodiment the comparison value is also formed in the calculation unit 432 by means of the measured expiratory flow and the reference value. In an embodiment of the invention, a health-related reference value indicating that the comparison value should not be lower than 50% is stored in the calculation unit 432. The calculation unit 432 compares the comparison value formed with the health-related reference value and the heart rate monitor indicates by means of the display means 326 via the central processor 424 by means of the display means 326 if the comparison value does not meet the health-related reference value. The calculation unit 432 preferably forms the threshold values of the stress parameters and compares the stress parameter and the threshold values of the stress parameters during the fitness exercise. The calculation unit 432 is connected to the central unit 424 via which the calculation unit 432 receives the values of input parameters needed for the calculations and comparison as well as information on the heart rate during the fitness exercise. The input parameters, such as physiological parameters, reference heart rate, health-related reference value, comparison value formed outside the heart rate monitor, one or more PEF values, are fed by means of the feeding means 324 of the heart rate monitor. The feeding means is e.g. a keypad, a speech controller, an optical connection, a radio link, a connecting cable or a telecommunications port for feeding information obtained from an external apparatus. It is clear that the calculation unit 432 does not need to be a separate device but its functions can be implemented in the central processor 424, for example.

In an embodiment of the invention the PEF meter is implemented in the heart rate monitor as shown in FIG. 4. In that case the value of expiratory flow measured by the PEF meter 300 included in the heart rate monitor is automatically supplied via the central processor 424 to the calculation unit 432, and thus the user does not need to feed the value with the feeding means 324 of the heart rate monitor.

The functions, means and models implementing the method steps of the invention are implemented by software for a general-purpose computer, as ASIC, by separate logic components or by any corresponding prior art manner. It is clear to a person skilled in the art that the heart rate monitor may also comprise other parts than those shown in FIG. 4, but it is irrelevant to describe them here.

Even though the invention has been described by means of examples according to the attached drawings, it is clear that the invention is not limited to them, but may be modified in various ways within the inventive concept defined in the appended claims.

What is claimed is:

1. A method of controlling a fitness exercise performed by a person, the method comprising:
   (a) measuring the person's heart rate information during the fitness exercise; and
   (b) informing the person if a value of a stress parameter formed from the measured heart rate information exceeds a threshold value formed for the stress parameter before the fitness exercise, wherein the threshold value of the stress parameter has been formed for the fitness exercise using the value of the person's expiratory flow.

2. A method according to claim 1, wherein the value of expiratory flow has been measured by a PEF meter.

3. A method according to claim 1, wherein the threshold value of the stress parameter has been formed on the basis of a comparison between the value of expiratory flow measured before the fitness exercise and the reference value of expiratory flow.

4. A method according to claim 3, wherein the reference value of expiratory flow is the person's maximal expiratory flow.

5. A method according to claim 3, wherein the reference value of expiratory flow has been formed by means of one or more physiological parameters which describe the person's physiological properties.

6. A method according to claim 1, wherein the stress parameter is the stress level and for forming the value of stress level during the fitness exercise one or more of the following parameters are used in addition to the heart rate information: one or more physiological parameters which describe the person's physiological properties, one or more stress parameters which describe the exercise workload.

7. A method according to claim 1, wherein the stress parameter is the heart rate level.

8. A method according to claim 1, wherein the person's expiratory flow measured is supplied to a heart rate monitor, which forms a threshold value for the stress parameter on the basis of the expiratory flow for controlling the fitness exercise.

9. A method according to claim 3, wherein the result of the comparison between the measured expiratory flow and the reference value of expiratory flow is compared with a health-related reference value, and if the comparison result does not meet the health-related reference value, the user is informed that it is not recommendable to exercise.

10. A method according to claim 1, wherein the person's heart rate is measured during the fitness exercise by the heart rate monitor and the stress parameter value is shown on the display of the heart rate monitor.

11. A heart rate monitor comprising:
   a measuring means for measuring the heart rate of a person during a fitness exercise;
   a calculation unit for forming the value of one or more stress parameters from the heart rate measured during the fitness exercise, the calculation unit being arranged to compare the stress parameter value during the fitness exercise with a threshold value formed for the stress parameter before the fitness exercise; and
   a display means for showing exceeding of the threshold parameter to the user during the fitness exercise,
   wherein the calculation unit is arranged to use a value of expiratory flow measured from the person before the fitness exercise for forming the threshold value of the stress parameter.

12. A heart rate monitor according to claim 11, wherein the calculation unit is arranged to use the stress level as the stress parameter during the fitness exercise and for forming the value of the stress parameter the calculation unit is arranged to use one or more of the following parameters in addition to the heart rate: one or more physiological parameters which describe the person's physiological properties, one or more stress parameters which describe the exercise workload.

13. A heart rate monitor according to claim 11, wherein the calculation unit is arranged to use the person's heart rate during the fitness exercise as the stress parameter.

14. A heart rate monitor according to claim 11, wherein the calculation unit is arranged to use the reference value of the person's expiratory flow for forming the threshold value of the stress parameter.

15. A heart rate monitor according to claim 14, wherein the reference value of expiratory flow is the person's maximal expiratory flow.

16. A heart rate monitor according to claim 14, wherein the calculation unit is arranged to form the reference value of expiratory flow by means of one or more physiological parameters which describe the person's physiological properties.

17. A heart rate monitor according to claim 11, wherein the display means includes at least one of:
   a sound signaling device;
   a voice messaging device;
   a vibrating device; and
   a display for showing the value of at least one of:
      one or more stress parameters; and
      the threshold value of the stress parameter.

18. A heart rate monitor according to claim 11, wherein the heart rate monitor comprises feeding means for feeding information used for forming the threshold value of the stress parameter in the calculation unit.

19. A heart rate monitor according to claim 14, wherein the calculation unit is arranged to form a comparison value between the measured expiratory flow and the reference value of expiratory flow and compare the comparison value with a health related reference value, the heart rate monitor being arranged to inform the person if the comparison value does not meet the health-related reference value.

20. A heart rate monitor according to claim 11, wherein the heart rate monitor comprises a PEF meter for measuring the expiratory flow.

* * * * *